United States Patent [19]

Nishino et al.

[11] 4,172,848

[45] Oct. 30, 1979

[54] PROCESS FOR MANUFACTURE OF 1,11-UNDECANEDIAMINE

[75] Inventors: Masaki Nishino; Yutaka Yasuhara, both of Nagoya, Japan

[73] Assignee: Toray Industries, Inc., Tokyo, Japan

[21] Appl. No.: 845,401

[22] Filed: Oct. 25, 1977

[30] Foreign Application Priority Data

Oct. 22, 1976 [JP] Japan .................................. 51-126299

[51] Int. Cl.$^2$ ...................... C07C 85/18; C07C 85/24
[52] U.S. Cl. .................................. 260/583 P; 260/690
[58] Field of Search ......... 260/583 P, 583 R, 239 BF, 260/580

[56] References Cited

U.S. PATENT DOCUMENTS

| | | | |
|---|---|---|---|
| 2,642,463 | 6/1953 | Arnold et al. | 260/585 C X |
| 3,412,156 | 11/1968 | Ueda et al. | 260/583 P |
| 3,941,717 | 3/1976 | Vollheim et al. | 260/580 X |
| 4,026,944 | 5/1977 | Bohm et al. | 260/580 |

FOREIGN PATENT DOCUMENTS

| | | | |
|---|---|---|---|
| 48-85511 | 11/1973 | Japan | 260/583 P |
| 995482 | 6/1965 | United Kingdom | 260/583 P |

OTHER PUBLICATIONS

Morrison et al., "Organic Chemistry," 2nd Edition, p. 636, (1966).
Augustine, "Catalytic Hydrogenation," p. 31, (1965).

*Primary Examiner*—Winston A. Douglas
*Assistant Examiner*—John Doll
*Attorney, Agent, or Firm*—Miller & Prestia

[57] ABSTRACT

A process for producing 1,11-undecanediamine by contacting 7-(5'-aminopentyl)-3,4,5,6-tetrahydro-2H-azepine and/or 1,11-diaminoundecanol-6 with hydrogen in the presence of a hydrogenation catalyst in a diluent comprising aqueous sulfuric acid.

25 Claims, No Drawings

PROCESS FOR MANUFACTURE OF 1,11-UNDECANEDIAMINE

This invention relates to the synthesis of 1,11-undecanediamine. More specifically, the invention relates to a process for conversion of 7-(5'-aminopentyl)-3,4,5,6-tetrahydro-2H-azepine, hereinafter referred to as Schiff's base (I) and represented by Formula I,

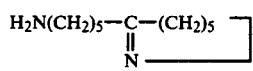

and/or 1,11-diaminoundecanol-6, hereinafter referred to as the amino-alcohol (II), and represented by Formula II,

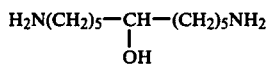

to 1,11-undecanediamine by catalytic hydrogenation.

The product of the present invention, 1,11-undecanediamine, is a very important raw material in synthetic chemical industries, particularly in the polymerization field which includes the manufacture of synthetic fibers or resins.

Heretofore, methods for producing the desired diamine have been disclosed as follows:

(i) catalytic hydrogenation of 1,11-diaminoundecene-4 or -5 (U.S. Pat. No. 3,412,156, issued Nov. 19, 1968 to Kanegafuchi Boseki);

(ii) reacting the Schiff's base (I) or its carbonate with hydrazine or its derivatives (French Pat. No. 1,372,867 issued Sep. 18, 1964; Japanese Patent Publication No. Sho. 40-12603 issued Jun. 21, 1965)

(iii) catalytic hydrogenation of a salt of 1,11-diaminoundecanone-6 with an inorganic acid such as hydrogen chloride or sulfuric acid over a platinum or rhodium-containing catalyst in glacial acetic acid containing an excess of the inorganic acid (Japanese Patent Publication No. Sho. 44-10524, published May 16, 1969).

In the process (i), complicated procedures are required in order to provide the necessary starting materials. In process (ii), a quantitative amount of costly hydrazine (or of a derivative) is consumed. Further, in process (iii), an unsatisfactorily low yield of the desired diamine is produced and at a rather slow reaction rate. This process also involves severe reaction conditions such as highly elevated pressures and temperatures, e.g., 100 atmospheres and 170° C. Furthermore, the use of acetic acid is inevitably accompanied by many deterrents of commercial utilization; the corrosive properties of acetic acid cause many difficulties, and the presence of a large quantity of the acidic solvent makes it complicated to isolate the alkaline product. Therefore, none of the foregoing processes has yet achieved commercial exploitation, so far as we are aware.

We have found that the Schiff's base (I) can be selectively hydrogenated to 1,11-undecanediamine at a relatively high reaction rate under specific hydrogenation conditions, as described below, in which particular diluent and inorganic acid employed, and hydrogenation catalyst provided are essential. By the practice of this invention 1,11-undecanediamine of high quality can be prepared in good yield.

The process of the present invention is effected in a diluent comprising aqueous sulfuric acid containing at least about 1.2 moles of sulfuric acid per mole of the Schiff's base (I) and/or the amino-alcohol (II) in the presence of a hydrogenation catalyst containing at least one component selected from the group consisting of metals of the platinum group and rhenium. Reaction conditions other than those of the present invention fail to accomplish the remarkable results attained by the present invention. Indeed, it has been reported in an operative example of the above mentioned Japanese Patent Publication No. Sho 44-10524, where glacial acetic acid saturated with hydrogen chloride is used as diluent, that a ruthenium catalyst exhibits no activity for conversion of 1,11-diaminoundecanone-6 to 1,11-undecanediamine. It is also found that when using sulfuric acid in glacial acetic acid under conditions similar to those in the above said Japanese patent, the formation of the desired product is retarded.

In Japanese Patent Publication No. Sho. 41-18096, published Oct. 18, 1966, it is disclosed that 2-(5'-aminopentyl)perhydroazepine, hereinafter referred to as the perhydroazepine (III), represented by Formula III,

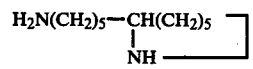

is produced by reaction of the Schiff's base (I) and hydrogen in a mixture of water and acetic acid in the presence of a Raney nickel catalyst and it failed to yield any substantial quantity of the desired product.

In accordance with the present invention, 1,11-undecanediamine can be produced from Schiff's base (I) and/or the amino-alcohol (II) in one step. The reaction process is believed to proceed in accordance with the following equations:

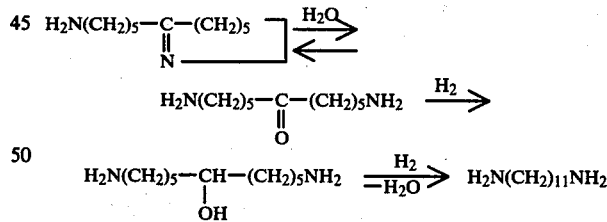

It should be noted that the amino-alcohol (II) is accordingly an intermediate in the preparation of the product.

The Schiff's base (I) is in equilibrium with 1,11-diaminoundecanone-6, as shown in the foregoing reaction diagram, in the presence of water. These compounds in equilibrium afford salts with acidic compounds such as sulfuric acid, phosphoric acid, hydrogen chloride, carbonic acid or carbon dioxide, or carboxylic acids. The salts can be isolated as salts of 1,11-diaminoundecanone-6 with most of the acidic compounds except carbonic acid or carbon dioxide; with those compounds a mixture of the carbamates represented by Formula IV,

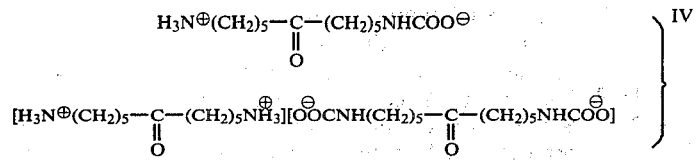

is isolated.

In accordance with the present invention, it is reasonable to use these salts as starting materials in place of Schiff's base (I) unless the acidic compound forming the salt should inhibit or retard the reaction of the invention. Such use includes this invention.

The Schiff's base (I) is produced by thermolysis of ε-caprolactam, ε-aminocaproic acid, or an oligomer or polymer thereof, in the presence of a hydroxide or oxide of an alkali metal or alkali earth metal such as lithium, calcium, etc. The amino-alcohol (II), another starting material is known to be produced by chemically reducing the Schiff's base (I) with an alkali metal hydroxide in a lower aliphatic hydroxy compound such as methanol, ethanol, etc. (U.S. Pat. No. 3,412,156). It can also be produced by partial catalytic hydrogenation of the Schiff's base (I) as disclosed here. The process of the present invention can be practiced in a diluent of aqueous sulfuric acid containing at least 1.2 moles of sulfuric acid per mole of the Schiff's base (I) and/or the amino-alcohol (II) in the reaction mixture. In general, the reaction proceeds even when smaller amounts of sulfuric acid are used, but the products of side reactions such as the perhydroazepine (III) and/or the amino-alcohol (II) may be predominant in some cases.

The upper limit of the amount of sulfuric acid can be quite high, e.g., ten or more moles per mole of the starting material, but no particular advantages are obtained in such a case. Therefore, from a practical viewpoint, the amount of sulfuric acid employed in the reaction mixture may be in an amount of from about 1.2 to 10 moles preferably in an amount of from about 1.5 to 8 moles, and more preferably about 2 to 5 moles per mole of Schiff's base (I) and/or the amino-alcohol (II) employed in the reaction mixture. As will be apparent from the specific examples disclosed hereinafter, the use of a bisulfate such as ammonium bisulfate, sodium bisulfate or potassium bisulfate, etc., is effective in the place of all or part of the sulfuric acid. In that case, it is recognized that two chemical equivalents of a bisulfate correspond to one mole of sulfuric acid.

The concentration of aqueous sulfuric acid in the reaction mixture is an important factor in the process of the invention. The concentration of the aqueous sulfuric acid used is not narrowly critical and can vary over a wide range. In general, at relatively higher concentrations, e.g., at concentrations as high as 70 weight percent and higher based on the total quantity of water and sulfuric acid, the rate of hydrogenation of a starting material may be extremely slow. On the other hand, at lower concentrations, the intermediate of the desired reaction, the amino-alcohol (II) may remain increasingly unreacted when starting from the Schiff's base (I), and therefore it is desirable to employ higher temperatures and/or a longer reaction time. At concentrations below 2 weight percent, the rate of desired product formation becomes quite slow. A suitable range of concentration of aqueous sulfuric acid is from about 2 weight percent to about 60 weight percent, preferably from about 5 weight percent to about 50 weight percent, based on the total quantity of water and sulfuric acid in the reaction mixture.

The invention is carried out in the presence of a hydrogenation catalyst having at least one component selected from the group consisting of metals of the platinum group and rhenium. Metals of the platinum group include ruthenium, rhodium, palladium, osmium, iridium, and platinum. Among these metals, rhenium, ruthenium, rhodium, osmium, iridium and platinum are preferred, when starting from the Schiff's base (I). Further, an increased reaction rate and/or higher conversion to the desired product can be obtained in the presence of ruthenium, osmium or iridium. The combined use of two or more of these metals is also effective. The hydrogenation catalyst may be used in optional forms, such as sponge, fine powder, colloid and supported form. Catalyst supports employed are, for example, silica, alumina, titania, charcoal, niobium pentoxide, tungsten trioxide, molybdenum trioxide, zeolites, asbestos, porous glass, silicon carbide, zirconia, barium sulfate and the like, and mixtures thereof as well as other suitable stable materials.

We have also discovered that the catalytic activity in reactions according to this invention may be promoted in the presence of a co-catalyst containing at least one component selected from the group consisting of metals of tungsten and molybdenum, when starting from Schiff's base (I). Illustrative co-catalysts which are generally suitable in the practice of desirable embodiments of the invention include, for example, metals or metal powders of tungsten or molybdenum, alloys containing tungsten or molybdenum, compounds of tungsten or molybdenum such as molybdic acid or its salts; tungstic acid or its salts; heteropolyacids or their salts such as phosphotungstic acid, phosphomolybdic acid or salts of either; tungsten oxide; molybdenum oxide; tungsten hexacarbonyl; molybdenum hexacarbonyl; and others.

The quantity of co-catalyst employed is not narrowly critical and can vary over a wide range. Usually, the co-catalyst component may be used in an amount of from about 0.01 to 100 parts preferably in an amount of from about 0.1 to 50 parts, by weight, based on the amount of the active metallic component of the hydrogenation catalyst.

The operative temperatures which may be employed can vary over a wide range of elevated temperatures. In general, the process can be conducted at a temperature in the range of about 80° C. and upwards to approximately 350° C. and higher. At the lower end of the temperature range, and below, the rate of reaction to form the desired product becomes markedly slow, and the formation of the intermediate of the reaction, the amino-alcohol (II) when starting from the Schiff's base (I) may be predominant. At relatively higher temperatures the activity of the catalyst used tends to become unstable. It is readily appreciated that the reaction temperature will be influenced, to a significant extent, by the concentration and amount of aqueous sulfuric acid, the reaction time and other factors. For example, using a relatively lower concentration of aqueous sulfuric acid, the process can be effected at relatively higher temperatures, and vice versa. Suitable operating temperatures can be between about 100° C. and about 300° C., and desirably from about 120° C. to about 250° C.

The process can be effected suitably over a wide range of hydrogen partial pressures of from about 1 to about 300 kilograms per square centimeter absolute. The pressure utilized will depend upon the reaction rate and the investment costs associated with erecting chemical plants with high pressure facilities. A preferred range of hydrogen partial pressures is from about 5 to about 150 atmospheres. The hydrogen employed need not be pure, but it can be diluted with inert gases such as nitrogen, argon, methane, etc.

The process can be executed in a batch, semi-continuous, or continuous fashion. The reaction can be conducted in a single reaction zone or a plurality of reaction zones, in series or in parallel, or it may be conducted intermittently or continuously in an elongated tubular zone or series of such zones. Catalysts may be introduced initially into the reaction zone batchwise, or may be continuously or intermittently introduced into such zone during the course of the synthesis reaction. Means to introduce and/or adjust the materials responsible for the reaction, either intermittently or continuously, into the reaction zone during the course of the reaction can be conveniently utilized in the process especially to maintain the desired molar ratios of, and the partial pressures of, the materials.

Isolation and purification of the desired product can be achieved by methods well-known in the art such as neutralization, concentration, phase-separation, extraction, crystallization, recrystallization, distillation, combinations thereof, and the like.

The following examples will serve to further illustrate the present invention. The terms "conversion" and "yield" used in the examples are defined as follows:

$$\text{Conversion (\%)} = \frac{\text{moles of starting material converted}}{\text{moles of starting material charged}}$$

$$\text{Yield (\%)} = \frac{\text{moles of product}}{\text{moles of starting material charged}}$$

EXAMPLE 1

Into a stirred solution of 160 g. of the Schiff's base (I) in 800 ml. ethanol and 80 ml. of water, a large excess of carbon dioxide was bubbled. The white precipitate was filtered with suction, washed with ethanol, and dried over anhydrous calcium chloride in vacuo. The product thus obtained weighed 165 g. and was the carbamate represented by Formula IV set forth above. The elementary analysis is as follows: Calculated for $C_{11}H_{24}N_2O_3$ C, 58.99; H, 9.90; N, 11.47. Found: C, 58.9; H, 10.2; N, 11.5.

Into a 35 ml. glass vessel having a coiled capillary vent were placed 1.0 g. of the above carbamate, 30 mg. of ruthenium black and 6 ml. of 24% (by weight) sulfuric acid, with the evolution of carbon dioxide. The vessel was placed in a 100 ml. stainless steel autoclave. After the inside of the autoclave was flushed with hydrogen, the autoclave was pressurized with hydrogen until a pressure of 50 atm. was reached, and heated by placing it in an oil bath. Stirring was provided by a bar magnet (sheathed with polytetrafluoroethylene) placed inside the vessel. The bar magnet was set in motion by an external magnetic stirrer. The temperature of the oil bath was maintained at 150° C. for 3.5 hours. Then, the autoclave was cooled to room temperature, and the hydrogen was vented. The reaction mixture, in which a certain amount of 1,12-dodecanediamine had been added as internal standard, was neutralized, and was made to an ethanolic solution after evaporating the water. The alcoholic solution was subjected to analysis by means of a gas chromatograph with the internal standard. This analysis proved that the carbamate had reacted to produce a 97% yield of 1,11-undecanediamine and a 2% yield of the perhydroazepine (III).

EXAMPLE 2

In a 25 ml. glass bomb capable of withstanding pressures up to 30 atm. were placed 0.5 g. of the Schiff's base (I), 50 mg. of a 5% ruthenium-on-silica gel catalyst, and 3 ml. of 24% sulfuric acid. The reaction was conducted in a manner similar to that set forth in Example 1, while maintaining a temperature of 150° C. and a pressure of 10 atm. of hydrogen for 3 hours. After venting the hydrogen, the reaction mixture was subjected to analysis by means of a gas chromatograph. The analysis showed that the Schiff's base (I) had reacted to produce a 98% yield of 1,11-undecanediamine and a less than 1% yield of the perhydroazepine (III).

EXAMPLE 3

In a manner similar to that set forth in Example 1, 1.0 g of the sulfate of 1,11-diaminoundecanone-6, produced by reacting equimolar amounts of the Schiff's base (I) and sulfuric acid, 200 mg. of a 5% ruthenium-on-silica gel catalyst and 6 ml. of 3 N sulfuric acid were treated with 50 atm. of hydrogen, at 150° C. for 3.5 hours. The analysis showed that a 96% yield of 1,11-undecanediamine was produced, with a yield of less than 1% of the perhydroazepine (III). Formation of a 1% yield of 1,11-diaminoundecanol-6 was confirmed.

EXAMPLE 4

Into a glass vessel of about 150 ml. capacity, possessing a coiled capillary vent were placed 13.5 g. of the Schiff's base (I), 202 mg. of a 5% ruthenium-on-silica gel catalyst, and 86 ml. of 5 N (about 21.3%) sulfuric acid. The vessel was placed in a 500 ml. stainless steel autoclave. The reaction was conducted as described in Example 2 except that the reaction time was 7 hours. After the reaction, 1 ml. aliquots of the reaction mixture were subjected to analysis by means of a gas chromatograph. The analysis showed that the Schiff's base (I) had reacted to produce 1,11-undecanediamine in a yield of more than 99% and the perhydroazepine (III) in a yield of less than 0.3%. On cooling the reaction mixture in an ice-water bath, 10.94 g. of the sulfate of 1,11-undecanediamine crystallized out as white needles. The gas chromatographic analysis showed that the sulfate had contained 63 weight percent of 1,11-undecanediamine. The carbamate used as starting material was the same as prepared in Example 1.

EXAMPLES 5-25

A series of examples were carried out by the process of the present invention. Reactions were conducted at a pressure of 50 atm. or 10 atm. in a manner similar to those set forth in Examples 1 and 2, respectively. The results of these experiments are shown in Table 1.

TABLE 1

| Example | Starting Material | Catalyst (mg.) | Concentration of aq. $H_2SO_4$(ml.) | Pressure (atm.) | Time (hr.) | Temperature (°C.) | Conversion (%) | Yield of 1,11-undecane-diamine (%) |
|---|---|---|---|---|---|---|---|---|
| 5 | carbamate (1.0g) | 5% Ru/SiO$_2$ (200) | 24% (wt.) (6) | 50 | 4 | 130 | 100 | 94 |
| 6 | carbamate (1.0g) | 5% Ru/SiO$_2$ (200) | 24% (wt.) (6) | 50 | 4 | 170 | 100 | 95 |
| 7 | carbamate (1.0g) | 5% Ru/C (200) | 24% (wt.) (6) | 50 | 3.5 | 150 | 100 | 98 |
| 8 | carbamate (1.0g) | 5% Ru/Al$_2$O$_3$ (100) | 24% (wt.) (6) | 50 | 3.5 | 150 | 100 | 90 |
| 9 | carbamate (1.0g) | RuO$_2$ (30) | 24% (wt.) (6) | 50 | 3.5 | 150 | 100 | 97 |
| 10 | carbamate (1.0g) | 5% Ir/SiO$_2$ (200) | 24% (wt.) (6) | 50 | 3.5 | 150 | 90 | 86 |
| 11 | carbamate (1.0g) | IrO$_2$ (30) | 24% (wt.) (6) | 50 | 3.5 | 150 | 100 | 97 |
| 12 | carbamate (1.0g) | 2% Os/SiO$_2$ (200) | 24% (wt.) (6) | 50 | 3.5 | 150 | 100 | 98 |
| 13 | carbamate (1.0g) | Re-black (30) | 24% (wt.) (6) | 50 | 3.5 | 150 | 41 | 35 |
| 14 | carbamate (1.0g) | 5% Pt/SiO$_2$ (200) | 24% (wt.) (6) | 50 | 3.5 | 150 | 59 | 52 |
| 15 | carbamate (1.0g) | 5% Pt/WO$_3$ (200) | 24% (wt.) (6) | 50 | 3.5 | 150 | 100 | 98 |
| 16 | carbamate (1.0g) | Rh$_2$O$_3$ (30) | 24% (wt.) (6) | 50 | 3.5 | 150 | 100 | 73 |
| 17 | carbamate (1.0g) | 5% Ru-Pd/SiO$_2$ (200) | 24% (wt.) (6) | 50 | 4 | 150 | 100 | 98 |
| 18 | carbamate (1.0g) | 5% Ru-Rh/SiO$_2$(200) | 24% (wt.) (6) | 50 | 4 | 150 | 100 | 90 |
| 19 | Schiff's base (0.45) | 5% Ru/SiO$_2$ (54) | 4.8% (10) | 10 | 8 | 180 | 100 | 84 |
| 20 | Schiff's base (0.45) | 5% Ru/SiO$_2$ (54) | 9.2% (6) | 10 | 6 | 150 | 100 | 90 |
| 21 | Schiff's base (0.45) | 5% Ru/SiO$_2$ (54) | 50% (1) | 10 | 6 | 130 | 100 | 99 |
| 22 | Schiff's base (0.45) | 5% Ru/SiO$_2$ (54) | 40% (0.75) | 10 | 17 | 160 | 100 | 90 |
| 23 | Schiff's base (0.45) | 5% Ru/SiO$_2$ (54) | 40% (3) | 10 | 17 | 100 | 91 | 87 |
| 24 | Schiff's base (0.45) | 5% Ru/SiC (15) | 24% (3) | 10 | 15 | 150 | 100 | 98 |
| 25 | Schiff's base (0.45) | 5% Ru/porous (3) glass | 24% (3) | 10 | 5 | 150 | 100 | 98 |

The following notes are applicable to Table 1:

In Example 17, the catalyst was prepared by mixing 0.84 g of ruthenium trichloride monohydrate, 0.21 g of palladium chloride and 66.7 g of "Snowtex N-20" (silica sol obtained from Nissan Kogyo Co., containing 30% SiO$_2$), evaporating the water to dryness on a hot bath in vacuo. The product was reduced in a stream of hydrogen at 150° C. for 5 hours, then allowed to stand under an atmosphere of ammonia for several hours at ambient temperature, then washed with water, and further reduced in a stream of hydrogen at 150° C. for 5 hours. The product was the desired catalyst containing 5 percent by total weight ruthenium and palladium in a ratio of 8:2.

In Example 18, the catalyst was prepared in a manner similar to that set forth in Example 17 by mixing ruthenium trichloride, rhodium trichloride and silica sol in amounts sufficient to provide a final catalyst containing 5 percent by total weight of ruthenium and rhodium in a ratio of 8:2.

EXAMPLE 26

This example was prepared in a manner similar to that set forth in Example 2, using 0.5 g of 1,11-diaminoundecanol-6, 50 mg. of a 5% ruthenium-on-silica gel catalyst, and 3 ml. of 24% sulfuric acid. The reaction was carried out at a temperature of 150° C. and under pressure of 10 atm. After a reaction period of 3.5 hours, the reaction mixture was subjected to analysis by means of a gas chromatograph. The analysis showed that a 96% yield of 1,11-undecanediamine had been produced.

EXAMPLES 27 and 28

These samples were prepared in a manner similar to that set forth in Example 2, using 0.45 g of Schiff's base (I), 25 mg. of a 5% ruthenium-on-silica gel catalyst, and an indicated amount of bisulfate dissolved in 3 ml. of water. The reaction was conducted for 20 hours, while maintaining a temperature of 170° C. and a pressure of 10 atm. The results are shown in Table 2, below:

Table 2

| Example | Bisulfate (g.) | Conversion (%) | Yield of 1,11-undecanediamine (%) |
|---|---|---|---|
| 27 | NH$_4$HSO$_4$ (1.5) | 100 | 88 |
| 28 | NaHSO$_4$ (1.8) | 100 | 86 |

In both examples, a small quantity of 1,11-diaminoundecanol-6 was detected.

EXAMPLE 29

This experiment was conducted in a manner similar to that set forth in Example 2, using 0.56 g of Schiff's base (I), 3.5 ml. of 21% (by weight) sulfuric acid, 30 mg. of platinum oxide and 24 mg. of molybdic acid monohydrate. The reaction was conducted while maintaining a temperature of 150° C. and a pressure of 10 atm. After a reaction period of 6 hours, the reaction mixture was subjected to analysis by means of a gas chromatograph. The analysis showed that the Schiff's base (I) had reacted to produce a 98% yield of 1,11-undecanediamine and a 0.4% yield of the perhydroazepine III.

EXAMPLES 30–49

A series of examples was carried out by the process of the present invention. Using 1 g. of the carbamate synthesized in Example 1, 6 ml. of 24 weight percent sulfuric acid, and indicated amounts of a catalyst and co-catalyst, reactions were conducted at a pressure of 50 atm. in a manner similar to that set forth in Example 1. Reaction conditions and the results of the reactions are shown in Table 3.

TABLE 3

| Example | Catalyst (mg.) | Co-Catalyst (mg.) | Temperature (°C.) | Time (hr) | Conversion (%) | Yield of 1,11-undecane-diamine (%) |
|---|---|---|---|---|---|---|
| 30 | PtO$_2$ (30) | H$_2$MoO$_4$ . H$_2$O (15) | 170 | 4 | 100 | 96 |
| 31 | PtO$_2$ (30) | H$_2$MoO$_4$ . H$_2$O (55) | 170 | 4 | 100 | 97 |
| 32 | PtO$_2$ (30) | H$_2$MoO$_4$ . H$_2$O (20) | 200 | 3 | 100 | 95 |
| 33 | PtO$_2$ (30) | H$_2$MoO$_4$ . H$_2$O (24) | 150 | 3.5 | 100 | 96 |
| 34 | PtO$_2$ (30) | H$_2$MoO$_4$ . H$_2$O (24) | 110 | 6 | 80 | 74 |

TABLE 3-continued

| Example | Catalyst (mg.) | Co-Catalyst (mg.) | Temperature (°C.) | Time (hr) | Conversion (%) | Yield of 1,11-undecane-diamine (%) |
|---|---|---|---|---|---|---|
| 35 | $PtO_2$ (15) | $Na_2WO_4 \cdot H_2O$ (22) | 130 | 6 | 100 | 96 |
| 36 | $PtO_2$ | $MoO_3$ (19) | 150 | 3.5 | 100 | 99 |
| 37 | $PtO_2$ (30) | phosphomolybdic acid (21) | 150 | 3.5 | 100 | 98 |
| 38 | $PtO_2$ (30) | $W(CO)_6$ (47) | 150 | 3.5 | 15 | 15 |
| 39 | $PtO_2$ (30) | $Mo(CO)_6$ (35) | 150 | 3.5 | 58 | 52 |
| 40 | $PtO_2$ (20) | $WO_3$ (31) | 150 | 3.5 | 65 | 65 |
| 41 | 5% $Pt/SiO_2$ (200) | $H_2MoO_4 \cdot H_2O$ (10) | 150 | 3.5 | 100 | 96 |
| 42 | Pt-black (30) | $H_2MoO_4 \cdot H_2O$ (20) | 150 | 3.5 | 100 | 97 |
| 43 | 5% $Pt/Al_2O_3$ (200) | $H_2MoO_4 \cdot H_2O$ (10) | 150 | 3.5 | 100 | 84 |
| 44 | 5% $Ru/SiO_2$ (200) | $H_2MoO_4 \cdot H_2O$ (10) | 150 | 3.5 | 100 | 97 |
| 45 | 5% Ru/C (200) | $H_2MoO_4 \cdot H_2O$ (15) | 150 | 3.5 | 100 | 97 |
| 46 | $Rh_2O_3$ (30) | $H_2MoO_4 \cdot H_2O$ (25) | 150 | 3.5 | 100 | 89 |
| 47 | 2% $Os/SiO_2$ (200) | $H_2MoO_4 \cdot H_2O$ (24) | 150 | 3.5 | 100 | 98 |
| 48 | $IrO_2$ (30) | $H_2MoO_4 \cdot H_2O$ (15) | 150 | 3.5 | 100 | 99 |
| 49 | 5% Ru-Pd/SiO(200) | $H_2MoO_4 \cdot H_2O$ (10) | 150 | 3.5 | 100 | 95 |

In Table 3, the following notes are applicable:

In Example 34, a yield of about 30% 1,11-diaminoundecanol-6 was detected. In Example 49, the catalyst is the same as that used in Example 17.

It will be appreciated that although certain specific forms of the invention have been referred to as examples herein, equivalents may be substituted therefor without departing from the spirit and scope of the invention as defined in the appended claims.

We claim:

1. A process for producing 1,11-undecanediamine which comprises contacting 7-(5'-aminopentyl)-3,4,5,6-tetrahydro-2H-azepine with hydrogen, in the presence of a hydrogenation catalyst containing at least one component selected from the group consisting of metals of the platinum group and rhenium, in a diluent consisting of aqueous sulfuric acid containing at least about 1.2 moles of sulfuric acid per mole of 7-(5'-aminopentyl)-3,4,5,6-tetrahydro-2H-azepine.

2. The process of claim 1 wherein said hydrogenation catalyst comprises at least one component selected from the group consisting of ruthenium, rhodium, palladium, osmium, iridium, platinum, rhenium and compounds thereof.

3. The process according to claim 1, wherein said hydrogenation catalyst comprises at least one component selected from the group consisting of ruthenium, rhodium, osmium, iridium, platinum, rhenium and compounds thereof.

4. The process of claim 1 wherein said hydrogenation catalyst comprises at least one component selected from the group consisting of ruthenium, osmium, iridium and compounds thereof.

5. The process of claim 1 wherein said diluent contains sulfuric acid in an amount of about 1.5 to 8 moles per mole of 7-(5'-aminopentyl)-3,4,5,6-tetrahydro-2H-azepine.

6. The process of claim 1 wherein the concentration of said aqueous sulfuric acid is in the range of about 5 weight percent to about 50 weight percent.

7. The process of claim 1 wherein said hydrogenation catalyst is carried on a support.

8. The process of claim 1 wherein said reaction is promoted in the presence of a co-catalyst comprising at least one component selected from the group consisting of tungsten, molybdenum and compounds thereof.

9. The process of claim 1 wherein the pressure of hydrogen is in the range of from about 1 to about 300 kilograms per square centimeter absolute.

10. The process of claim 1 wherein the reaction temperature is in the range of from about 80° C. to about 350° C.

11. A process for producing 1,11-undecanediamine which comprises contacting 1,11-diaminoundecanol-6 with hydrogen in the presence of a hydrogenation catalyst comprising at least one component selected from the group consisting of metals of the platinum group and rhenium, in a diluent consisting of aqueous sulfuric acid containing at least about 1.2 moles of sulfuric acid per mole of 1,11-diaminoundecanol-6.

12. The process of claim 11 wherein said hydrogenation catalyst contains at least one component selected from the group consisting of ruthenium, rhodium, palladium, osmium, iridium, platinum, rhenium and compounds thereof.

13. The process of claim 11 wherein said sulfuric acid is present in an amount of from about 1.5 to 8 moles per mole of 1,11-diaminoundecanol-6 employed in the reaction mixture.

14. The process of claim 11 wherein the concentration of said aqueous sulfuric acid is in the range of from about 5 weight percent to about 50 weight percent.

15. The process of claim 11 wherein said hydrogenation catalyst is carried on a support.

16. The process of claim 11 wherein the pressure of hydrogen is in the range of from about 1 to about 300 kilograms per square centimenter absolute.

17. The process of claim 11 wherein the reaction temperature is in the range of from about 80° C. to about 350° C.

18. A process for producing 1,11-undecanediamine which comprises contacting 7-(5'-aminopentyl)-3,4,5,6-tetrahydro-2H-azepine with hydrogen, in the presence of a hydrogenation catalyst containing at least one component selected from the group consisting of metals of the platinum group and rhenium, in a diluent containing an acidic sulfate selected from the group consisting of (I) aqueous sulfuric acid containing at least about 1.2 moles of sulfuric acid per mole of 7-(5'-aminopentyl)-3,4,5,6-tetrahydro-2H-azepine and (II) a bisulfate such as ammonium bisulfate, sodium bisulfate or potassium bisulfate, two chemical equivalents of which correspond to one mole of sulfuric acid, and (III) mixtures of (I) and (II).

19. The process defined in claim 18 wherein the amount of said acidic sulfate is chemically equivalent to 1.2-10 moles of sulfuric acid per mole of said azepine.

20. The process defined in claim 18 wherein the amount of said acidic sulfate is chemically equivalent to 1.5–8 moles of sulfuric acid per mole of said azepine.

21. The process defined in claim 18 wherein the amount of said acidic sulfate is chemically equivalent to 2–5 moles of sulfuric acid per mole of said azepine.

22. A process for producing 1,11-undecanediamine which comprises contacting 1,11-diaminoundecanol-6 with hydrogen in the presence of a hydrogenation catalyst comprising at least one component selected from the group consisting of metals of the platium group and rhenium, in a diluent consisting of an acidic sulfate selected from the group consisting of (I) aqueous sulfuric acid containing at least about 1.2 moles of sulfuric acid per mole of 1,11-diaminoundecanol-6 and (II) a bisulfate such as ammonium bisulfate, sodium bisulfate or potassium bisulfate, two chemical equivalents of which correspond to one mole of sulfuric acid, and (III) mixtures of (I) and (II).

23. The process defined in claim 22 wherein the amount of said acidic sulfate is chemically equivalent to 1.2–10 moles of sulfuric acid per mole of 1,11-diaminoundecanol-6.

24. The process defined in claim 22 wherein the amount of said acidic sulfate is chemically equivalent to 1.5–8 moles of sulfuric acid per mole of 1,11-diaminoundecanol-6.

25. The process defined in claim 22 wherein the amount of said acidic sulfate is chemically equivalent to 2–5 moles of sulfuric acid per mole of 1,11-diaminoundecanol-6.

* * * * *

UNITED STATES PATENT AND TRADEMARK OFFICE
CERTIFICATE OF CORRECTION

PATENT NO. : 4,172,848
DATED : October 30, 1979
INVENTOR(S) : Masaki Nishino et al It is certified that error appears in the above-identified patent and that said Letters Patent are hereby corrected as shown below:

Col. 7, line 7, Example 8 of Table 1, under the column identified as "Catalyst (mg.)", "5% $Ru/Al_2O_3$ (100)" should read --5% $Ru/Al_2O_3$ (200)--.

Cols. 9 and 10, line 5, Example 36,

| Catalyst (mg.) | Co-Catalyst (mg.) | Temperature (°C) | Time (hr) | Conversion (%) | Yield of 1,11-undecanediamine (%) |
|---|---|---|---|---|---|
| "$PtO_2MoO_3$ (19) | 150 | 3.5 | 100 | 99 | " | should read as

| | | | | | |
|---|---|---|---|---|---|
| --$PtO_2$ (30) | $MoO_3$ (19) | 150 | 3.5 | 100 | 99 -- |

Signed and Sealed this

Twenty-second Day of January 1980

[SEAL]

Attest:

SIDNEY A. DIAMOND

Attesting Officer

Commissioner of Patents and Trademarks